US011763461B2

(12) United States Patent
Ma et al.

(10) Patent No.: US 11,763,461 B2
(45) Date of Patent: Sep. 19, 2023

(54) SPECIMEN CONTAINER CHARACTERIZATION USING A SINGLE DEEP NEURAL NETWORK IN AN END-TO-END TRAINING FASHION

(71) Applicant: Siemens Healthcare Diagnostics Inc., Tarrytown, NY (US)

(72) Inventors: Kai Ma, West Windsor, NJ (US); Yao-Jen Chang, Princeton, NJ (US); Terrence Chen, Princeton, NJ (US); Benjamin S. Pollack, Jersey City, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 376 days.

(21) Appl. No.: 17/251,756

(22) PCT Filed: Jun. 10, 2019

(86) PCT No.: PCT/US2019/036351
§ 371 (c)(1),
(2) Date: Dec. 11, 2020

(87) PCT Pub. No.: WO2019/241134
PCT Pub. Date: Dec. 19, 2019

(65) Prior Publication Data
US 2021/0164965 A1 Jun. 3, 2021

Related U.S. Application Data

(60) Provisional application No. 62/685,344, filed on Jun. 15, 2018.

(51) Int. Cl.
*G06T 7/12* (2017.01)
*G01N 33/49* (2006.01)
(Continued)

(52) U.S. Cl.
CPC .............. *G06T 7/12* (2017.01); *G01N 33/49* (2013.01); *G01N 35/04* (2013.01);
(Continued)

(58) Field of Classification Search
CPC ... G06T 7/12; G06T 7/70; G06T 2207/20081; G06T 2207/20084; G06T 7/174;
(Continued)

(56) References Cited

U.S. PATENT DOCUMENTS 9,322,761 B2   4/2016  Miller
10,198,832 B2  2/2019  De Fauw et al.
(Continued)

FOREIGN PATENT DOCUMENTS

CN   105825509 A   8/2016
CN   106372390 A   2/2017
(Continued)

OTHER PUBLICATIONS

PCT International Search Report and Written Opinion dated Aug. 29, 2019 (7 Pages).
(Continued)

*Primary Examiner* — Bobbak Safaipour

(57) ABSTRACT

A method of characterizing a serum or plasma portion of a specimen in a specimen container includes capturing a plurality of images of the specimen container from multiple viewpoints, stacking the multiple viewpoint images along a channel dimension into a single stacked input, and processing the stacked input with a single deep convolutional neural network (SDNN). The SDNN includes a segmentation convolutional neural network that receives the stacked input and outputs multiple label maps simultaneously. The SDNN also includes a classification convolutional neural network that processes the multiple label maps and outputs an HILN determination (Hemolysis, Icterus, and/or Lipemia, or Nor-
(Continued)

mal) of the serum or plasma portion of the specimen. Quality check modules and testing apparatus configured to carry out the method are also described, as are other aspects.

20 Claims, 7 Drawing Sheets

(51) Int. Cl.
*G06T 7/70* (2017.01)
*G16H 10/40* (2018.01)
*G01N 35/04* (2006.01)
*G06F 18/2431* (2023.01)

(52) U.S. Cl.
CPC ............ *G06F 18/2431* (2023.01); *G06T 7/70* (2017.01); *G16H 10/40* (2018.01); *G01N 2035/0406* (2013.01); *G01N 2035/0493* (2013.01); *G06T 2207/20081* (2013.01); *G06T 2207/20084* (2013.01)

(58) Field of Classification Search
CPC ................... G01N 33/49; G01N 35/04; G01N 2035/0406; G01N 2035/0493; G06F 18/2431; G16H 10/40
See application file for complete search history.

(56) References Cited

U.S. PATENT DOCUMENTS

| | | | |
|---|---|---|---|
| 2017/0364771 A1 | 12/2017 | Pinheiro et al. | |
| 2018/0045654 A1 | 2/2018 | Park et al. | |
| 2020/0158745 A1* | 5/2020 | Tian | G06V 10/143 |
| 2021/0064927 A1* | 3/2021 | Kluckner | G06F 18/24133 |
| 2021/0133971 A1* | 5/2021 | Ma | B01L 9/06 |
| 2021/0334972 A1* | 10/2021 | NarasimhaMurthy | G01N 35/00732 |

FOREIGN PATENT DOCUMENTS

| | | |
|---|---|---|
| CN | 106408562 A | 2/2017 |
| CN | 108596166 A | 9/2018 |
| JP | 2019-500110 A | 1/2019 |
| JP | 2019-531463 A | 10/2019 |
| JP | 2019-531783 A | 11/2019 |
| JP | 2019-537011 A | 12/2019 |
| JP | 2021-510201 A | 4/2021 |
| WO | 2016/133900 A1 | 8/2016 |
| WO | 2017/106645 A1 | 6/2017 |
| WO | 2018/022280 A1 | 2/2018 |
| WO | 2018/039380 A1 | 3/2018 |
| WO | 2018/089938 A1 | 5/2018 |
| WO | 2018/105062 A1 | 6/2018 |
| WO | 2018/188023 A1 | 10/2018 |
| WO | 2018/191287 A1 | 10/2018 |
| WO | 2019/241128 A1 | 12/2019 |

OTHER PUBLICATIONS

Deshpande, Adit, "A Beginner's Guide to Understanding Convolutional Neural Networks Part 1", 13 pages (Jul. 20, 2016).
Deshpande, Adit, "A Beginner's Guide to Understanding Convolutional Neural Networks Part 2", 6 pages (Jul. 29, 2016).
Jegou, Simon et al., "The One Hundred Layers Tiramisu: Fully Convolutional DenseNets for Semantic Segmentation"; arXiv:1611.09326v3 [cs.CV] Oct. 31, 2017, 9 pages.
Simonyan, Karen, et al., "Very Deep Convolutional Networks for Large-Scale Image Recognition"; Published as a conference paper at ICLR 2015; arXiv:1409.1556v6 [cs.CV] Apr. 10, 2015, pp. 1-14.
Extended EP Search Report dated Oct. 19, 2021 of corresponding European Application No. 19819602.4, 5 Pages.
Hideki, Aso: Deep Representation Learning by Multi-Layer Neural Networks; the Japanese Society for Artificial Intelligence; Year: Jul. 2013, vol. 28 No. 4, pp. 649-659.
Shaoqing Ren et al., Faster R-CNN: Towards Real-Time Object Detection with Region Proposal Networks, Computer Vision and Computer Recognition, Jan. 6, 2016, arXiv:1506.01497.
Lecun, Yann et al., Gradient-based learning applied to document recognition, Proceedings of the IEEE, Nov. 1998, vol. 86, Issue No. 11.
For understanding of basis of convolutional neural network, Jul. 25, 2018, https://www.imagazine.co.jp/%E7%95%B3%E3%81%BF%E8%BE%BC%E3%81%BF%E3%83%8D%E3%83%83%E3%83%88%E3%83%AF%E3%83%BC%E3%82%AF%E3%81%AE%E3%80%8C%E5%9F%BA%E7%A4%8E%E3%81%AE%E5%9F%BA%E7%A4%8E%E3%80%8D%E3%82%92%E7%90%86%E8%A7%A3%E3%81%99/.
For understanding of basis of convolutional neural network, Jun. 7, 2021 https://leadinge.co. convolutional neural networkjp/rd/2021/06/07/863/.
Convolutional neural network https://ml4a.github.io/ml4a/jp/convnets/.

\* cited by examiner

SPECIMEN CONTAINER CHARACTERIZATION USING A SINGLE DEEP NEURAL NETWORK IN AN END-TO-END TRAINING FASHION

CROSS-REFERENCE TO RELATED APPLICATIONS

This application claims priority to U.S. Provisional Application Ser. No. 62/685,344 filed on Jun. 15, 2018, the contents of which is incorporated herein by reference in its entirety.

FIELD

This disclosure relates to methods and apparatus for characterizing a specimen container (and specimen therein) in an automated diagnostic analysis system.

BACKGROUND

Automated diagnostic analysis systems may conduct assays or clinical analyses using one or more reagents to identify an analyte or other constituent in a specimen such as urine, blood serum, blood plasma, interstitial liquid, cerebrospinal liquid, and the like. Such specimens are usually contained within specimen containers (e.g., specimen collection tubes). The testing reactions generate various changes that may be read and/or manipulated to determine a concentration of an analyte or other constituent in the specimen.

Improvements in automated testing technology have been accompanied by corresponding advances in pre-analytical specimen preparation and handling operations such as sorting, batch preparation, centrifuging of specimen containers to separate specimen components, cap removal to facilitate fluid access, pre-screening for HILN (Hemolysis, Icterus, and/or Lipemia, or Normal), and the like by automated specimen preparation systems called Laboratory Automation Systems (LASs). LASs may also automatically transport a specimen in a specimen container to a number of specimen processing stations so various operations (e.g., pre-analytical or analytical testing) can be performed thereon.

LASs may handle a number of different specimens contained in standard, barcode-labeled specimen containers, which may be of different sizes (e.g., diameters and heights). The barcode label may contain an accession number that may contain or be correlated to patient information and other information that may have been entered into a hospital's Laboratory Information System (LIS) along with test orders. An operator may place the labeled specimen containers onto the LAS system, which may automatically route the specimen containers for pre-analytical operations such as centrifugation, de-capping, and/or aliquot preparation before the specimen is subjected to clinical analysis or assaying by one or more analyzers (e.g., clinical chemistry or assaying instruments) that may also be part of the LAS.

For certain tests, a biological liquid such as a serum or plasma portion (obtained from whole blood by centrifugation) may be analyzed. Where the specimen is whole blood, a gel separator may be added to the specimen container to aid in the separation of a settled blood portion from the serum or plasma portion. After pre-processing, the specimen container may be transported to an appropriate analyzer that may extract a portion of the biological fluid (e.g., serum or plasma portion) from the specimen container and combine the fluid with one or more reagents and possibly other materials in a reaction vessel (e.g., a cuvette). Analytical measurements may then be performed via photometric or fluorometric absorption readings by using a beam of interrogating radiation or the like. The measurements allow determination of end-point rate or other values, from which an amount of an analyte or other constituent in the biological fluid is determined using well-known techniques.

However, the presence of any interferent (e.g., Hemolysis, Icterus, and/or Lipemia) in the specimen, which may result from a patient condition or sample processing, may adversely affect test results of the analyte or constituent measurement obtained from the one or more analyzers. For example, the presence of hemolysis (H) in the specimen, which may be unrelated to a patient's disease state, may cause a different interpretation of the disease condition of the patient. Moreover, the presence of icterus (I) and/or lipemia (L) in the specimen may also cause a different interpretation of the disease condition of the patient.

In some systems, a skilled laboratory technician may visually inspect and rate the integrity of the serum or plasma portion of the specimen as either normal (N) or as having a degree of H, I, and/or L (e.g., by assigning an index). This may involve a review of the color of the serum or plasma portion against known standards. However, such manual visual inspection is very subjective, labor intensive, and fraught with possible human error.

Because manual inspection may be problematic, efforts have been made to evaluate specimen integrity without the use of visual inspection by a laboratory technician, but rather by using an automated machine-vision inspection apparatus, wherein such evaluation takes place during pre-analytical testing (hereinafter "pre-screening"). The pre-screening involves automated detection of an interferent, such as H, I, and/or L, in a serum or plasma portion obtained from whole blood by fractionation (e.g., by centrifugation).

However, in some instances, one or more of the above-described barcode-labels may be affixed directly on the specimen container. Such labels may partially occlude and obscure certain lateral viewpoints of the specimen, so that there may be some orientations that do not provide a clear opportunity to visually observe the serum or plasma portion. Thus, automation of such pre-screening has included, for example, rotationally orienting the specimen in such a way that allows for automated pre-screening for H, I, and/or L or N (see e.g., U.S. Pat. No. 9,322,761). In other systems, the specimen container and specimen are imaged from multiple viewpoints and processed with model-based systems so that rotation of the specimen container is not needed (see, e.g., WO 2016/133,900).

In some instances, only a small portion of the serum or plasma portion may be visible, so that any H, I, and/or L, or N reading taken on the serum or plasma portion may not involve a high level of confidence. Moreover, such systems may be complicated and processing of the image data may be computationally burdensome.

Accordingly, there is an unmet need for a robust and efficient method and apparatus for characterizing a serum or plasma portion of a specimen in order to determine a presence of hemolysis (H), icterus (I), and/or lipemia (L), or whether the serum or plasma portion of the specimen is normal (N). More particularly, there is an unmet need for improved methods and apparatus for determining if a specimen includes H, I, and/or L or is normal (N).

SUMMARY

According to a first aspect, a method of characterizing a specimen container is provided. The method includes capturing multiple images of the specimen container from multiple viewpoints wherein the specimen container includes a serum or plasma portion of a specimen therein; inputting image data from the multiple images to a segmentation convolutional neural network and processing the image data with the segmentation convolutional neural network to simultaneously output multiple label maps; inputting the multiple label maps to a classification convolutional neural network and processing the multiple label maps with the classification convolutional neural network; and outputting from the classification convolutional neural network a classification of the serum or plasma portion as being one or more of hemolytic, icteric, lipemic, or normal.

According to another aspect, a quality check module is provided. The quality check module includes a plurality of image capture devices configured to capture multiple images from multiple viewpoints of a specimen container containing a serum or plasma portion of a specimen therein, and a computer coupled to the plurality of image capture devices. The computer is configured and operative to: input image data from the multiple images to a segmentation convolutional neural network and process the image data with the segmentation convolutional neural network to simultaneously output multiple label maps, input the multiple label maps to a classification convolutional neural network and process the multiple label maps with the classification convolutional neural network, and output from the classification convolutional neural network a classification of the serum or plasma portion as being one or more of hemolytic, icteric, lipemic, or normal.

In a further aspect, a specimen testing apparatus is provided. The specimen testing apparatus includes a track, a carrier moveable on the track and configured to contain a specimen container containing a serum or plasma portion of a specimen therein, a plurality of image capture devices arranged around the track and configured to capture multiple images from multiple viewpoints of the specimen container and the serum or plasma portion of the specimen, and a computer coupled to the plurality of image capture devices. The computer is configured and operative to: input image data from the multiple images to a segmentation convolutional neural network and process the image data with the segmentation convolutional neural network to simultaneously output multiple label maps, input the multiple label maps to a classification convolutional neural network and process the multiple label maps with the classification convolutional neural network; and output from the classification convolutional neural network a classification of the serum or plasma portion as being one or more of hemolytic, icteric, lipemic, or normal.

Still other aspects, features, and advantages of this disclosure may be readily apparent from the following description by illustrating a number of example embodiments and implementations, including the best mode contemplated for carrying out the invention. This disclosure may also be capable of other and different embodiments, and its several details may be modified in various respects, all without departing from the scope of the invention. This disclosure is intended to cover all modifications, equivalents, and alternatives falling within the scope of the appended claims (see further below).

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

DETAILED DESCRIPTION

Figure 1:
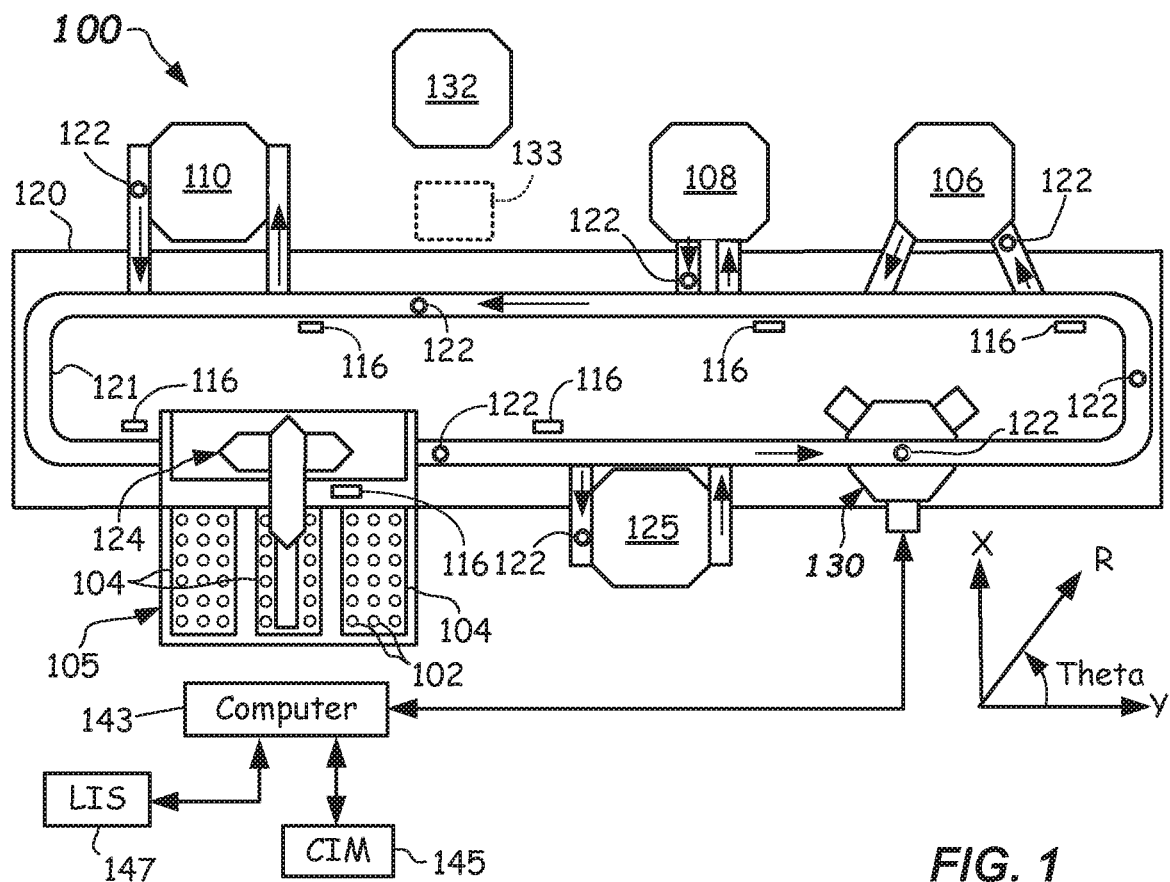
FIG. 1 illustrates a top schematic view of a specimen testing apparatus including one or more quality check modules configured to carry out HILN detection methods according to one or more embodiments.

During pre-screening of a specimen contained in a specimen container, such as at a quality check module described further below, a method is provided in accordance with embodiments that determines the presence of an interferent in the serum or plasma portion of the specimen. The serum or plasma portion may be the liquid component of blood and may be found above the settled blood portion after fractionation (e.g., by centrifugation). The settled blood portion may be a packed semi-solid made up of blood cells such as white blood cells (leukocytes), red blood cells (erythrocytes), and platelets (thrombocytes). Plasma and serum may differ from each other in the content of coagulating components, primarily fibrinogen. Plasma may be the un-clotted liquid, whereas serum may refer to blood plasma that has been allowed to clot either under the influence of endogenous enzymes or exogenous components.

An interferent, such as H, I, and/or L, or a determination of normal (N) (hereinafter "HILN"), as used herein refers to the presence of at least one of hemolysis (H), icterus (I), or lipemia (L) in the serum or plasma portion of the specimen. "N" refers to "normal," which may be defined as a serum or plasma portion that includes acceptably low amounts of H, I, and L. Hemolysis may be defined as a condition in the serum or plasma portion wherein red blood cells are destroyed during processing, which leads to the release of hemoglobin from the red blood cells into the serum or plasma portion such that the serum or plasma portion takes on a reddish hue. The degree of hemolysis may be quantified by assigning a Hemolytic Index. Icterus may be defined as a condition of the blood where the serum or plasma portion is discolored dark yellow, caused by an accumulation of bile pigment (bilirubin). The degree of icterus may be quantified by assigning an Icteric Index. Lipemia may be defined as a presence in the blood of an abnormally high concentration of emulsified fat, such that the serum or plasma portion has a whitish or milky appearance. The degree of lipemia may be quantified by assigning a Lipemic Index.

The method in accordance with embodiments may determine just HILN or N-Class H (e.g., H1, H2, H3, or more), N-Class I (e.g., I1, I2, I3, or more), and/or N-Class L (e.g., L1, L2, L3, or more), or N. In addition, the method may classify (or "segment") various regions of the specimen container and specimen, such as serum or plasma portion, settled blood portion, gel separator (if used), air, label, type of specimen container (indicating, e.g., height and width/diameter), and/or type and/or color of a specimen container cap. A specimen container holder or background may also be classified. Differentiation of the serum and plasma portion from the region comprising one or more labels on the specimen container is a particularly vexing problem, because the one or more labels may wrap around the specimen container to various degrees. Thus, the one or more labels may obscure one or more views, such that a clear view of the serum or plasma portion may be difficult to obtain.

Thus, classification of the serum or plasma portion may be challenging due to interference from the one or more labels, whose placement may vary substantially from one specimen container to the next. In particular, the obstruction caused by the one or more labels may heavily influence the spectral responses, such as from various viewpoints, given that the one or more labels may appear on a back side and thus may affect light transmission received at a front side.

Moreover, the quality check module of an automated diagnostic analysis system and associated characterization method performed therein should be computationally efficient. Accordingly, given the challenges described above, in a first broad aspect, embodiments of this disclosure provide methods and apparatus configured to determine the presence of HILN using a single semantic segmentation convolutional neural network (SCNN) whose output is coupled as input to a classification convolutional neural network (CONN), which are collectively referred to herein as a single deep neural network (SDNN). The SDNN may include a large number of operational layers (e.g., 50-100; other numbers of operational layers are possible), described further below.

In some embodiments, the input to the SCNN may be multi-spectral, multi-exposure image data, which may be consolidated and normalized, and obtained from a plurality of image capture devices. An image capture device may be any device capable of capturing a pixelated image (e.g., digital image) for analysis, such as a digital camera, a CCD (charge-coupled device), one or more CMOS (complementary metal-oxide semiconductor) sensors, an array of sensors, or the like. The plurality of image capture devices may be arranged and configured to capture images from multiple viewpoints (e.g., three viewpoints; other numbers of viewpoints are possible). The methods described herein may use high dynamic range (HDR) image processing of the specimen container and serum or plasma portion as an input to the SCNN. HDR imaging may involve capturing multiple exposures while using multiple spectral illuminations. In some embodiments, the SCNN is trained to recognize regions occluded by one or more labels on the specimen container so that the SCNN can better account for the presence of labels on the back side of the specimen container from any viewpoint in characterizing HILN.

As a result, more effective classification of the serum or plasma region may be available in cases where label obstruction is present, and the confidence in the intensity readings for those regions of the serum or plasma portion that are occluded by a label can be improved. Thus, an improved determination of HILN and/or the extent of HIL can be output from the SDNN.

The specimen may be collected in a specimen container, such as a blood collection tube and may include a settled blood portion and a serum and plasma portion after fractionation (e.g., separation by centrifugation). In some specimen containers, a gel separator may be used, which positions itself between the settled blood portion and the serum or plasma portion during centrifugation. The gel separator serves as a physical barrier between the two portions (liquid and semi-solid, settled blood cells), and may minimize remixing thereof. The specimen containers may be of different sizes and thus may be supplied for pre-screening and to the analyzers in a number of different configurations. For example, the specimen containers may have sizes such as 13 mm×75 mm, 13 mm×100 mm, 16 mm×100 mm, and 16 mm×125 mm. Other suitable sizes may be used.

In accordance with one aspect, the characterization method may be carried out by a quality check module, and in specimen testing systems, each including the SDNN. The SDNN may include operational layers including, e.g., BatchNorm, ReLU activation, convolution (e.g., 2D), dropout, and deconvolution (e.g., 2D) layers to extract features, such as simple edges, texture, and parts of the serum or plasma portion and label-containing regions. Top layers, such as fully convolutional layers, may be used to provide correlation between parts. The output of the layer may be fed to a SoftMax layer, which produces an output on a per pixel (or per patch—including n×n pixels) basis concerning whether each pixel or patch includes HILN. In some embodiments, only an output of HILN is provided from the CCNN. In other embodiments, the output of the CCNN may be fine-grained HILN, such as H1, H2, H3, I1, I2, I3, L1, L2, L3, or N, so that for each interferent present an estimate of the level (index) of the interferent is also obtained.

Should the specimen be found to contain one or more of H, I, and L, a suitable notice may be provided to the operator, and/or the specimen container may be taken off line (1) to perform a remediation to rectify the one or more of the H, I, or L, (2) to more accurately measure an extent of the interferent present, (3) to redraw the specimen, or (4) to perform other processing. Thus, the ability to pre-screen for HILN, such as at the first possible instance after centrifugation, and before analysis by one or more analyzers, may advantageously (a) minimize time wasted analyzing specimens that are not of the proper quality for analysis, (b) may avoid or minimize erroneous test results, (c) may minimize patient test result delay, and/or (d) may avoid wasting of patient specimen.

In some embodiments, combinations of segmentation output and HILN output may be provided. The outputs may result from multiple branches of the SDNN. The branches may include separate convolutional layers and deconvolution and SoftMax layers, wherein one branch may be dedicated to segmentation and the other to HILN detection.

Multi-branch embodiments including HILN, segmentation, specimen container type detection, and/or cap type detection may also be provided.

Further details of inventive characterization methods, quality check modules configured to carry out the characterization methods, and specimen testing apparatus including one or more quality check modules will be further described with reference to FIGS. 1-8 herein.

Figure 2:
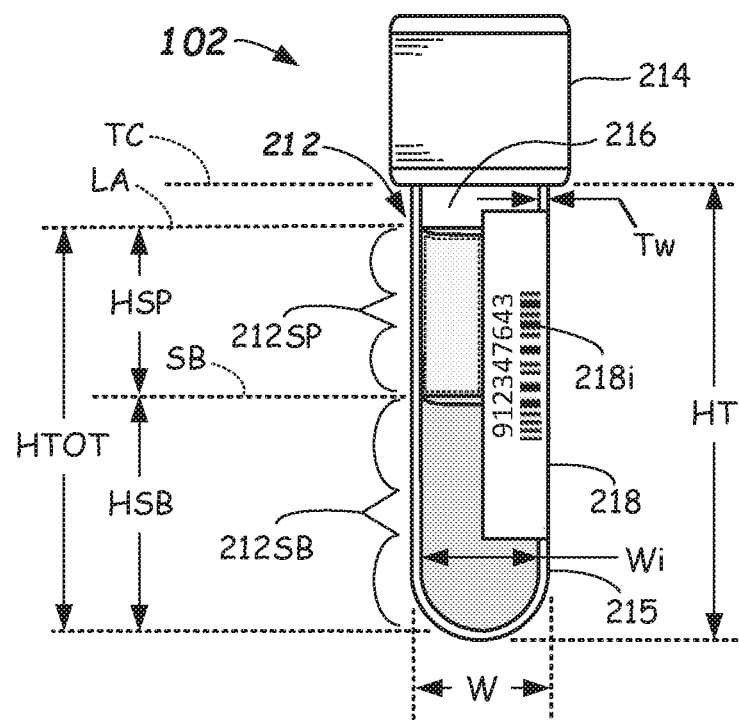
FIG. 2 illustrates a side view of a specimen container including a separated specimen with a serum or plasma portion containing an interferent, and wherein the specimen container includes a label thereon.
Figures 3A, 3B:
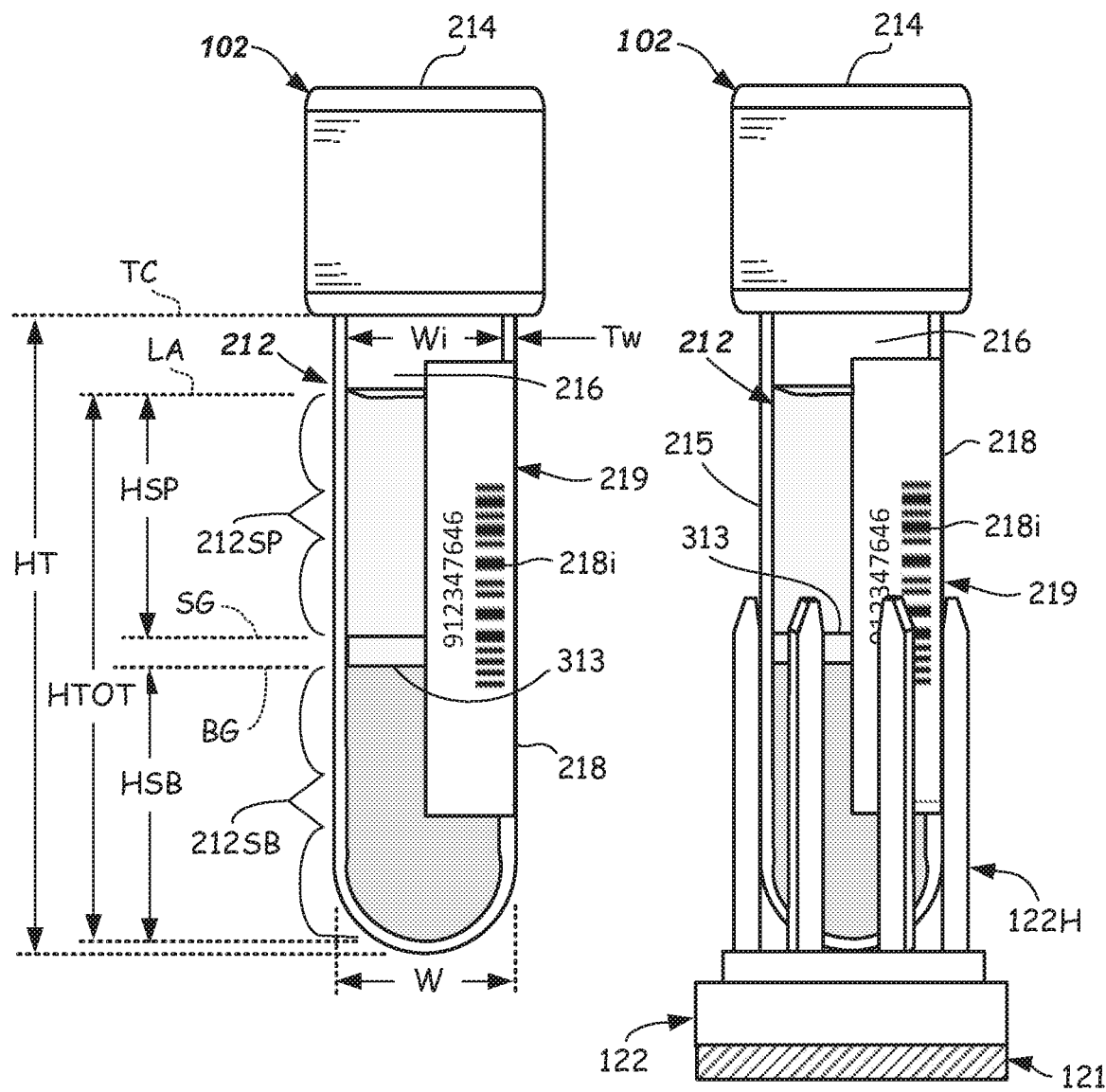
FIG. 3A illustrates a side view of a specimen container including a label, a separated specimen including a serum or plasma portion containing an interferent, and a gel separator therein.
FIG. 3B illustrates a side view of the specimen container of FIG. 3A held in an upright orientation in a holder.

FIG. 1 illustrates a specimen testing apparatus 100 capable of automatically processing multiple specimen containers 102 containing specimens 212 (see, e.g., FIGS. 2-3B). The specimen containers 102 may be provided in one or more racks 104 at a loading area 105 prior to transportation to, and analysis by, one or more analyzers (e.g., first, second, and third analyzer 106, 108, and/or 110, respectively) arranged about the specimen testing apparatus 100. More or less numbers of analyzers can be used. The analyzers may be any combination of clinical chemistry analyzers and/or assaying instruments, or the like. The specimen containers 102 may be any suitably transparent or translucent container, such as a blood collection tube, test tube, sample cup, cuvette, or other clear or opaque glass or plastic container capable of containing and allowing imaging of the specimen 212 contained therein. The specimen containers 102 may be varied in size.

Specimens 212 (FIGS. 2-3B) may be provided to the specimen testing apparatus 100 in the specimen containers 102, which may be capped with a cap 214. The caps 214 may be of different types and/or colors (e.g., red, royal blue, light blue, green, grey, tan, yellow, or color combinations), which may have meaning in terms of what test the specimen container 102 is used for, the type of additive included therein, whether the container includes a gel separator, or the like. Other colors may be used. In one embodiment, the cap type may be determined by the characterization method described herein.

Each of the specimen containers 102 may be provided with a label 218, which may include identification information 218*i* (i.e., indicia) thereon, such as a barcode, alphabetic, numeric, or combination thereof. The identification information 218*i* may be machine readable at various locations about the specimen testing apparatus 100. The machine readable information may be darker (e.g., black) than the label material (e.g., white paper) so that it can be readily imaged. The identification information 218*i* may indicate, or may otherwise be correlated, via a Laboratory Information System (LIS) 147, to a patient's identification as well as tests to be performed on the specimen 212. The identification information 218*i* may indicate other or additional information. Such identification information 218*i* may be provided on the label 218, which may be adhered to or otherwise provided on an outside surface of the tube 215. As shown in FIG. 2, the label 218 may not extend all the way around the specimen container 102 or all along a length of the specimen container 102 such that from the particular front viewpoint shown, a large part of the serum or plasma portion 212SP is viewable (the part shown dotted) and unobstructed by the label 218.

However, in some embodiments, multiple labels 218 may have been provided (such as from multiple facilities that have handled the specimen container 102), and they may overlap each other to some extent. For example, two labels (e.g., a manufacturer's label and a barcode label) may be provided and may be overlapping and may occlude (obstruct) some or all of one or more viewpoints.

Thus, it should be understood that in some embodiments, although the label(s) 218 may occlude some portion of the specimen 212 (an occluded portion), some portion of the specimen 212 and serum and plasma portion 212SP may still be viewable from at least one viewpoint (an un-occluded portion). Thus, in accordance with another aspect of the disclosure, embodiments of the SDNN configured to carry out the characterization method can be trained to recognize the occluded and un-occluded portions, such that improved HILN detection may be provided.

Again referring to FIG. 2, the specimen 212 may include the serum or plasma portion 212SP and a settled blood portion 212SB contained within the tube 215. Air 216 may be provided above the serum and plasma portion 212SP and a line of demarcation between them is defined as the liquid-air interface (LA). The line of demarcation between the serum or plasma portion 212SP and the settled blood portion 212SB is defined as a serum-blood interface (SB). An interface between the air 216 and cap 214 is defined as a tube-cap interface (TC). The height of the tube (HT) is defined as a height from a bottom-most part of the tube 215 to a bottom of the cap 214, and may be used for determining tube size. A height of the serum or plasma portion 212SP is (HSP) and is defined as a height from a top of the serum or plasma portion 212SP to a top of the settled blood portion 212SB. A height of the settled blood portion 212SB is (HSB) and is defined as a height from the bottom of the settled blood portion 212SB to a top of the settled blood portion 212SB at SB. HTOT is a total height of the specimen 212 and equals HSP plus HSB.

In cases where a gel separator 313 is used (FIG. 3A), the height of the serum or plasma portion 212SP is (HSP) and is defined as a height from the top of the serum or plasma portion 212SP at LA to the top of the gel separator 313 at SG, wherein SG is an interface between the serum or plasma portion 212SP and the gel separator 313. A height of the settled blood portion 212SB is (HSB) and is defined as a height from the bottom of the settled blood portion 212SB to the bottom of the gel separator 313 at BG, wherein BG is an interface between the settled blood portion 212SB and the gel separator 313. HTOT is the total height of the specimen 212 and equals HSP plus HSB plus height of the gel separator 313. In each case, Tw is a wall thickness, W is an outer width, which may also be used for determining the size of the specimen container 102, and Wi is an inner width of the specimen container 102.

In more detail, specimen testing apparatus 100 may include a base 120 (FIG. 1) (e.g., a frame, floor, or other structure) upon which a track 121 may be mounted. The track 121 may be a railed track (e.g., a mono rail or a multiple rail), a collection of conveyor belts, conveyor chains, moveable platforms, or any other suitable type of conveyance mechanism. Track 121 may be circular or any other suitable shape and may be a closed track (e.g., endless track) in some embodiments. Track 121 may, in operation, transport individual ones of the specimen containers 102 to various locations spaced about the track 121 in carriers 122.

Carriers 122 may be passive, non-motored pucks that may be configured to carry a single specimen container 102 on the track 121, or optionally, an automated carrier including an onboard drive motor, such as a linear motor that is programmed to move about the track 121 and stop at pre-programmed locations. Other configurations of carrier 122 may be used. Carriers 122 may each include a holder 122H (FIG. 3B) configured to hold the specimen container 102 in a defined upright position and orientation. The holder 122H may include a plurality of fingers or leaf springs that secure the specimen container 102 on the carrier 122, but some may be moveable or flexible to accommodate different sizes of the specimen containers 102. In some embodiments, carriers 122 may leave from the loading area 105 after being offloaded from the one or more racks 104. The loading area 105 may serve a dual function of also allowing reloading of the specimen containers 102 from the carriers 122 to the loading area 105 after pre-screening and/or analysis is completed.

A robot 124 may be provided at the loading area 105 and may be configured to grasp the specimen containers 102 from the one or more racks 104 and load the specimen containers 102 onto the carriers 122, such as onto an input lane of the track 121. Robot 124 may also be configured to reload specimen containers 102 from the carriers 122 to the one or more racks 104. The robot 124 may include one or more (e.g., least two) robot arms or components capable of X (lateral) and Z (vertical—out of the paper, as shown), Y and Z, X, Y, and Z, or r (radial) and theta (rotational) motion. Robot 124 may be a gantry robot, an articulated robot, an R-theta robot, or other suitable robot wherein the robot 124 may be equipped with robotic gripper fingers oriented, sized, and configured to pick up and place the specimen containers 102.

Upon being loaded onto track 121, the specimen containers 102 carried by carriers 122 may progress to a first pre-processing station 125. For example, the first pre-processing station 125 may be an automated centrifuge configured to carry out fractionation of the specimen 212. Carriers 122 carrying specimen containers 102 may be diverted to the first pre-processing station 125 by inflow lane or other suitable robot. After being centrifuged, the specimen containers 102 may exit on outflow lane, or otherwise be removed by a robot, and continue along the track 121. In the depicted embodiment, the specimen container 102 in carrier 122 may next be transported to a quality check module 130 to carry out pre-screening, as will be further described herein with reference to FIGS. 4A-8 herein.

The quality check module 130 is configured to pre-screen and carry out the characterization methods described herein, and is configured to automatically determine a presence of, and possibly an extent of H, I, and/or L contained in a specimen 212 or whether the specimen is normal (N). If found to contain effectively-low amounts of H, I and/or L, so as to be considered normal (N), the specimen 212 may continue on the track 121 and then may be analyzed by the one or more analyzers (e.g., first, second, and/or third analyzers 106, 108, and/or 110). Thereafter, the specimen container 102 may be returned to the loading area 105 for reloading to the one or more racks 104.

In some embodiments, in addition to detection of HILN, segmentation of the specimen container 102 and specimen 212 may take place. From the segmentation data, post processing may be used for quantification of the specimen 212 (i.e., determination of HSP, HSB, HTOT, and determination of location of SB or SG, and LA). In some embodiments, characterization of the physical attributes (e.g., size—height and width/diameter) of the specimen container 102 may take place at the quality check module 130. Such characterization may include determining HT and W, and possibly TC, and/or Wi. From this characterization, the size of the specimen container 102 may be extracted. Moreover, in some embodiments, the quality check module 130 may also determine cap type, which may be used as a safety check and may catch whether a wrong tube type has been used for the test ordered.

In some embodiments, a remote station 132 may be provided on the specimen testing apparatus 100 that is not directly linked to the track 121. For instance, an independent robot 133 (shown dotted) may carry specimen containers 102 containing specimens 212 to the remote station 132 and return them after testing/pre-processing. Optionally, the specimen containers 102 may be manually removed and returned. Remote station 132 may be used to test for certain constituents, such as a hemolysis level, or may be used for further processing, such as to lower a lipemia level through one or more additions and/or through additional processing, or to remove a clot, bubble or foam, for example. Other pre-screening using the HILN detection methods described herein may be accomplished at remote station 132.

Additional station(s) may be provided at one or more locations on or along the track 121. The additional station(s) may include a de-capping station, aliquoting station, one or more additional quality check modules 130, and the like.

The specimen testing apparatus 100 may include a number of sensors 116 at one or more locations around the track 121. Sensors 116 may be used to detect a location of specimen containers 102 on the track 121 by means of reading the identification information 218i, or like information (not shown) provided on each carrier 122. Any suitable means for tracking the location may be used, such as proximity sensors. All of the sensors 116 may interface with the computer 143, so that the location of each specimen container 102 may be known at all times.

The pre-processing stations and the analyzers 106, 108, 110 may be equipped with robotic mechanisms and/or inflow lanes configured to remove carriers 122 from the track 121, and with robotic mechanisms and/or outflow lanes configured to reenter carriers 122 to the track 121.

Specimen testing apparatus 100 may be controlled by the computer 143, which may be a microprocessor-based central processing unit CPU, having a suitable memory and suitable conditioning electronics and drivers for operating the various system components. Computer 143 may be housed as part of, or separate from, the base 120 of the specimen testing apparatus 100. The computer 143 may operate to control movement of the carriers 122 to and from the loading area 105, motion about the track 121, motion to and from the first pre-processing station 125 as well as operation of the first pre-processing station 125 (e.g., centrifuge), motion to and from the quality check module 130 as well as operation of the quality check module 130, and motion to and from each analyzer 106, 108, 110 as well as operation of each analyzer 106, 108, 110 for carrying out the various types of testing (e.g., assay or clinical chemistry).

For all but the quality check module 130, the computer 143 may control the specimen testing apparatus 100 according to software, firmware, and/or hardware commands or circuits such as those used on the Dimension® clinical chemistry analyzer sold by Siemens Healthcare Diagnostics Inc. of Tarrytown, N.Y. and such control is typical to those skilled in the art of computer-based electromechanical control programming and will not be further described herein. However, other suitable systems for controlling the specimen testing apparatus 100 may be used. The control of the quality check module 130 may also be provided by the computer 143, but in accordance with the inventive characterization methods described in detail herein.

The computer 143 used for image processing and to carry out the characterization methods described herein may include a CPU or GPU, sufficient processing capability and RAM, and suitable storage. In one example, the computer 143 may be a multi-processor-equipped PC with one or more GPUs, 8 GB Ram or more, and a Terabyte or more of storage. In another example, the computer 143 may be a GPU-equipped PC, or optionally a CPU-equipped PC operated in a parallelized mode. MKL could be used as well, 8 GB RAM or more, and suitable storage.

Embodiments of the disclosure may be implemented using a computer interface module (CIM) 145 that allows a user to easily and quickly access a variety of control and status display screens. These control and status display screens may display and enable control of some or all aspects of a plurality of interrelated automated devices used for preparation and analysis of specimens 212. The CIM 145 may be employed to provide information about the operational status of a plurality of interrelated automated devices as well as information describing the location of any specimen 212, as well as a status of tests to be performed on, or being performed on, the specimen 212. The CIM 145 is thus adapted to facilitate interactions between an operator and the specimen testing apparatus 100. The CIM 145 may include a display screen operative to display a menu including icons, scroll bars, boxes, and buttons through which the operator may interface with the specimen testing apparatus 100. The menu may comprise a number of function elements programmed to display and/or operate functional aspects of the specimen testing apparatus 100.

Figure 4A:
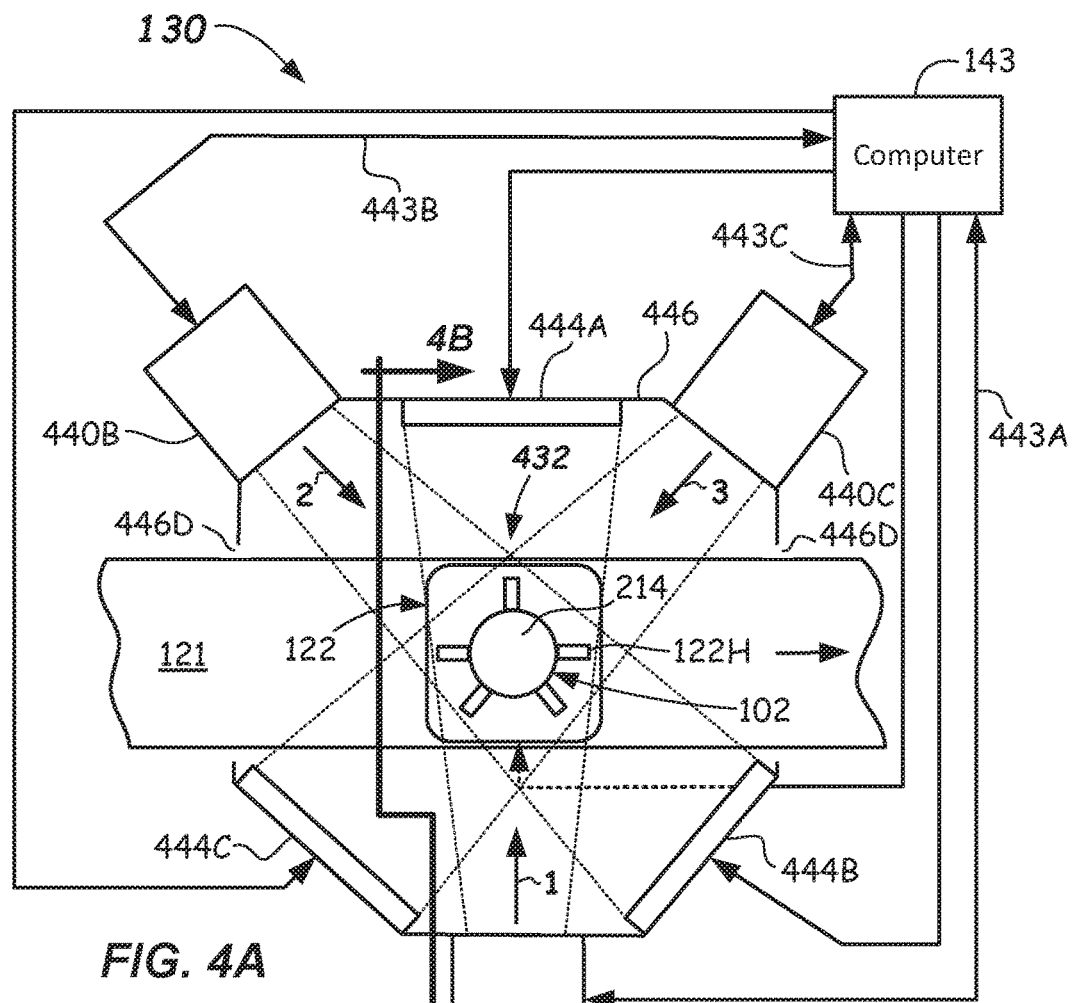
FIG. 4A illustrates a schematic top view of a quality check module (with top removed) including multiple viewpoints and configured to capture and analyze multiple backlit images to enable a determination of a presence of an interferent according to one or more embodiments.
Figure 4B:
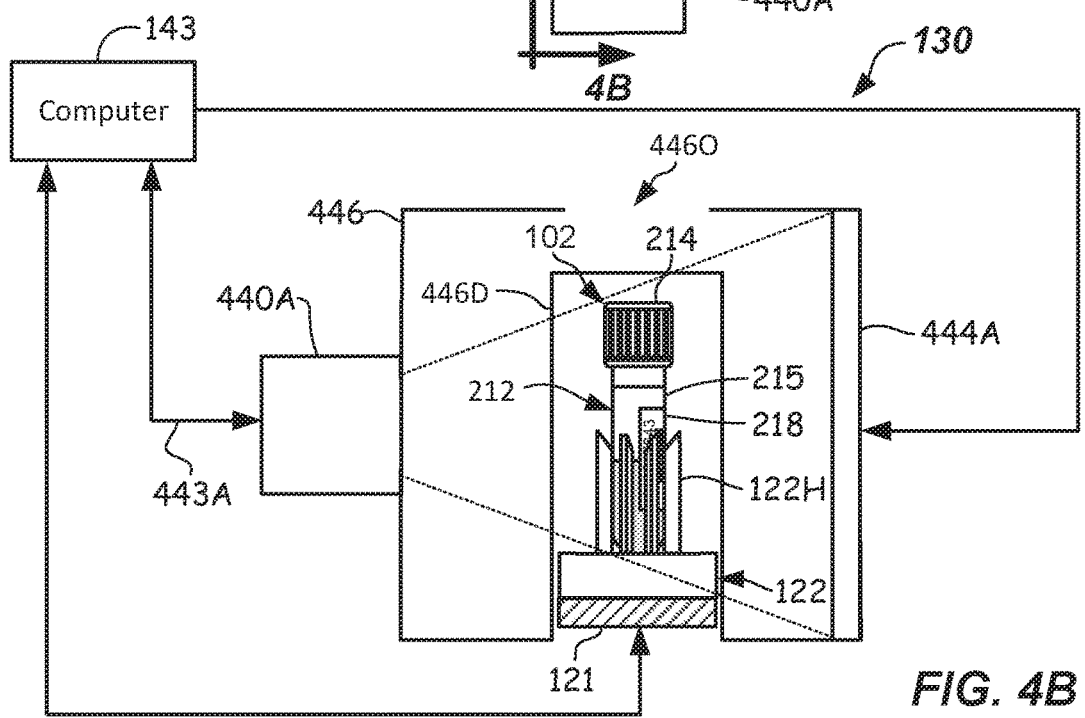
FIG. 4B illustrates a schematic side view of the quality check module (with front enclosure wall removed) of FIG. 4A taken along section line 4B-4B of FIG. 4A according to one or more embodiments.

FIGS. 4A and 4B show a first embodiment of a quality check module 130 configured to carry out the characterization methods as shown and described herein. Quality check module 130 may be configured to pre-screen for presence of an interferent (e.g., H, I, and/or L) in a specimen 212 (e.g., in a serum or plasma portion 212SP thereof) prior to analysis by the one or more analyzers 106, 108, 110. Pre-screening in this manner allows for additional processing, additional quantification or characterization, and/or discarding and/or redrawing of a specimen 212 without wasting valuable analyzer resources or possibly having the presence of an interferent affect the veracity of the test results.

In addition to the interferent detection methods described herein, other detection methods may take place on the specimen 212 contained in the specimen container 102 at the quality check module 130. For example, a method may be carried out at the quality check module 130 to provide segmentation as an output from the SDNN. The segmentation data may be used in a post processing step to quantify the specimen 212, i.e., determine certain physical dimensional characteristics of the specimen 212 (e.g., LA and SB, and/or determination of HSP, HSB, and/or HTOT). Quantification may also involve estimating, e.g., a volume of the serum or plasma portion (VSP) and/or a volume of the settled blood portion (VSB). Other quantifiable geometrical features may also be determined.

Furthermore, the quality check module 130 may be used to quantify geometry of the specimen container 102, i.e., quantify certain physical dimensional characteristics of the specimen container 102, such as the location of TC, HT, and/or W or Wi of the specimen container 102.

Referring to FIGS. 1, 4A, and 4B, the quality check module 130 may include multiple image capture devices 440A-440O. Three image capture devices 440A-440C are shown and are preferred, but optionally two or four or more can be used. Image capture devices 440A-440O may be any suitable device for capturing well-defined digital images, such as conventional digital cameras capable of capturing a pixelated image, charged coupled devices (CCD), an array of photodetectors, one or more CMOS sensors, or the like. For example, the three image capture devices 440A, 440B, 440C are illustrated in FIG. 4A and are configured to capture images from three different lateral viewpoints (viewpoints labeled 1, 2, and 3). The captured image size may be, e.g., about 2560×694 pixels. In another embodiment, the image capture devices 440A, 440B, 440C may capture an image size that may be about 1280×387 pixels, for example. Other image sizes and pixel densities may be used.

Each of the image capture devices 440A, 440B, 440C may be configured and operable to capture lateral images of at least a portion of the specimen container 102, and at least a portion of the specimen 212. For example, the image capture devices 440A-440O may capture a part of the label 218 and part or all of the serum or plasma portion 212SP. In some instances, e.g., part of a viewpoint 1-3 may be partially occluded by label 218. In some embodiments, one or more of the viewpoints 1-3 may be fully occluded, i.e., no clear view of the serum or plasma portion 212SP may be possible. However, even in cases where a side (front side or back side) of a viewpoint 1-3 is fully occluded by one or more labels 218, the characterization method may still be able to distinguish the boundaries of the serum or plasma portion 212SP through the one or more occluding labels 218.

In the embodiment shown, the plurality of image capture devices 440A, 440B, 440C are configured to capture lateral images of the specimen container 102 and specimen 212 at an imaging location 432 from the multiple viewpoints 1-3. The viewpoints 1-3 may be arranged so that they are approximately equally spaced from one another, such as about 120° from one another, as shown. As depicted, the image capture devices 440A, 440B, 440C may be arranged around the track 121. Other arrangements of the plurality of image capture devices 440A, 440B, 440C may be used. In this way, the images of the specimen 212 in the specimen container 102 may be taken while the specimen container 102 is residing in the carrier 122 at the imaging location 432. The field of view of the multiple images obtained by the image capture devices 440A, 440B, 440C may overlap slightly in a circumferential extent.

In one or more embodiments, the carriers 122 may be stopped at a pre-determined location in the quality check module 130, such as at the imaging location 432, i.e., such as at a point where normal vectors from each of the image capture devices 440A, 440B, 440C intersect each other. A gate or the linear motor of the carrier 122 may be provided to stop the carriers 122 at the imaging location 432, so that multiple quality images may be captured thereat. In an embodiment where there is a gate at the quality check module 130, one or more sensors (like sensors 116) may be used to determine the presence of a carrier 122 at the quality check module 130.

The image capture devices 440A, 440B, 440C may be provided in close proximity to and trained or focused to capture an image window at the imaging location 432, wherein the image window is an area including an expected location of the specimen container 102. Thus, the specimen container 102 may be stopped so that it is approximately located in a center of the view window in some embodiments. Within the images captured, one or more reference datum may be present.

In operation of the quality check module 130, each image may be triggered and captured responsive to a triggering signal provided in communication lines 443A, 443B, 443C that may be sent by the computer 143. Each of the captured images may be processed by the computer 143 according to one or more embodiments. In one particularly effective method, high dynamic range (HDR) processing may be used to capture and process the image data from the captured images. In more detail, multiple images are captured of the specimen 212 at the quality check module 130 at multiple different exposures (e.g., at different exposure times), while being sequentially illuminated at one or more different spectra. For example, each image capture device 440A, 440B, 440C may take 4-8 images of the specimen container 102 including the serum or plasma portion 212SP at different exposure times at each of multiple spectra. For example, 4-8 images may be taken by image capture device 440A at viewpoint 1 while the specimen 212 is backlit illuminated with light source 444A that has a red spectrum. Additional like images may be taken sequentially at viewpoints 2 and 3.

In some embodiments, the multiple spectral images may be accomplished using different light sources 444A-444C emitting different spectral illumination. The light sources 444A-444C may back light the specimen container 102 (as shown). A light diffuser may be used in conjunction with the light sources 444A-444C in some embodiments. The multiple different spectra light sources 444A-444C may be RGB light sources, such as LEDs emitting nominal wavelengths of 634 nm+/−35 nm (Red), 537 nm+/−35 nm (Green), and 455 nm+/−35 nm (Blue). In other embodiments, the light sources 444A-444C may be white light sources. In cases where the label 218 obscures multiple viewpoints, IR backlighting or NIR backlighting may be used. Furthermore, RGB light sources may be used in some instances even when label occlusion is present. In other embodiments, the light sources 444A-444C may emit one or more spectra having a nominal wavelength between about 700 nm and about 1200 nm.

By way of a non-limiting example, to capture images at a first wavelength, three red light sources 444A-444C (wavelength of about 634 nm+/−35 nm) may be used to sequentially illuminate the specimen 212 from three lateral locations. The red illumination by the light sources 444A-444C may occur as the multiple images (e.g., 4-8 images or more) at different exposure times are captured by each image capture device 440A-4400 from each viewpoint 1-3. In some embodiments, the exposure times may be between about 0.1 ms and 256 ms. Other exposure times may be used. In some embodiments, each of the respective images for each image capture device 440A-4400 may be taken sequentially, for example. Thus, for each viewpoint 1-3, a group of images are sequentially obtained that have red spectral backlit illumination and multiple (e.g., 4-8 exposures, such as different exposure times). The images may be taken in a round robin fashion, for example, where all images from viewpoint 1 are taken followed sequentially by viewpoints 2 and 3.

In each embodiment, the quality check module 130 may include a housing 446 that may at least partially surround or cover the track 121 to minimize outside lighting influences. The specimen container 102 may be located inside the housing 446 during the image-taking sequences. Housing 446 may include one or more doors 446D to allow the carriers 122 to enter into and/or exit from the housing 446. In some embodiments, the ceiling may include an opening 446O to allow a specimen container 102 to be loaded into the carrier 122 by a robot including moveable robot fingers from above.

Once the red illuminated images are captured in the embodiment of FIGS. 4A-4B, another spectra of light, for example, green spectral light sources 444A-444C may be turned on (nominal wavelength of about 537 nm with a bandwidth of about +/−35 nm), and multiple images (e.g., 4-8 or more images) at different exposure times may be sequentially captured by each image capture device 440A, 440B, 440C. This may be repeated with blue spectral light sources 444A-4440 (nominal wavelength of about 455 nm with a bandwidth of about +/−35 nm) for each image capture devices 440A, 440B, 440C. The different nominal wavelength spectral light sources 444A-444C may be accomplished by light panels including banks of different desired spectral light sources (e.g., R, G, B, W, IR, and/or NIR) that can be selectively turned on and off, for example. Other means for backlighting may be used.

The multiple images taken at multiple exposures (e.g., exposure times) for each respective wavelength spectra may be obtained in rapid succession, such that the entire collection of backlit images for the specimen container 102 and specimen 212 from multiple viewpoints 1-3 may be obtained in less than a few seconds, for example. In one example, four different exposure images for each wavelength at three viewpoints 1-3 using the image capture devices 440A, 440B, 440C and back lighting with RGB light sources 444A-444C will result in 4 images×3 spectra×3 image capture devices=36 images. In another example, 4 different exposure images for each wavelength at three viewpoints using the image capture devices 440A, 440B, 440C and back lighting with R, G, B, W, IR, and NIR light sources 444A-444C will result in 4 images×6 spectra×3 cameras=72 images.

According to embodiments of the characterization methods, the processing of the image data may involve a pre-processing step including, for example, selection of optimally-exposed pixels from the multiple captured images at the different exposure times at each wavelength spectrum and for each image capture device 440A-440C, so as to generate optimally-exposed image data for each spectrum and for each viewpoint 1-3. This is referred to as "image consolidation" herein.

For each corresponding pixel (or patch), for each of the images from each image capture device 440A-440C, pixels (or patches) exhibiting optimal image intensity may be selected from each of the different exposure images for each viewpoint 1-3. In one embodiment, optimal image intensity may be pixels (or patches) that fall within a predetermined range of intensities (e.g., between 180-254 on a scale of 0-255), for example. In another embodiment, optimal image intensity may be between 16-254 on a scale of 0-255), for example. If more than one pixel (or patch) in the corresponding pixel (or patch) locations of two exposure images is determined to be optimally exposed, the higher of the two is selected.

The selected pixels (or patches) exhibiting optimal image intensity may be normalized by their respective exposure times. The result is a plurality of normalized and consolidated spectral image data sets for the illumination spectra (e.g., R, G, B, white light, IR, and/or IR—depending on the combination used) and for each image capture device 440A-440C where all of the pixels (or patches) are optimally exposed (e.g., one image data set per spectrum) and normalized. In other words, for each viewpoint 1-3, the data pre-processing carried out by the computer 143 results in a plurality of optimally-exposed and normalized image data sets, one for each illumination spectra employed.

Figure 5:
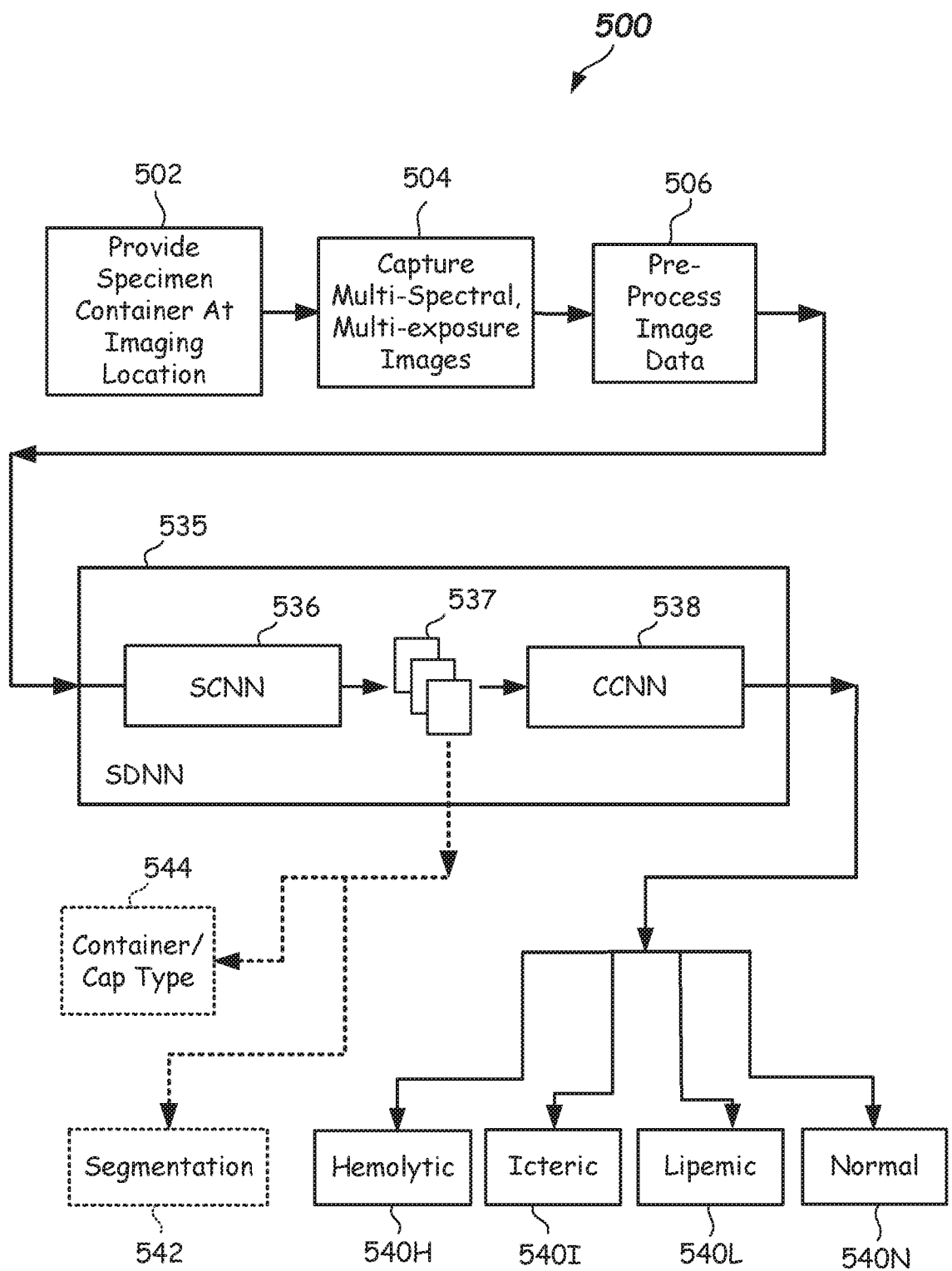
FIG. 5 illustrates a block diagram of functional components of a quality check module including a single deep convolutional neural network (SDNN) configured to determine a presence of H, I, and/or L or N in a specimen according to one or more embodiments.

FIG. 5 shows apparatus 500 that includes functional components configured carry out the HILN characterization method described herein. Apparatus 500 may be embodied as a quality check module 130 controlled by the computer 143. As discussed above, the specimen container 102 may be provided at the imaging location 432 (FIGS. 4A and 4B) of the quality check module 130 in functional block 502. The multi-view images are captured in functional block 504 by the plurality of image capture devices 440A-440C. The image data for each of the multi-view, multi-spectral, multi-exposure images may be pre-processed in functional block 506 as discussed above to provide a plurality of optimally-exposed and normalized image data sets (hereinafter "image data sets"). Moreover, in some embodiments, respective image data from each of the plurality of image capture devices 440A-440O may be stacked, or correlated, as a single input with additional channels corresponding to the number of image capture devices (e.g., three times more channels corresponding to the three image capture devices 440A-440O). For example, images from the three image capture devices 440A-440C may be stacked along the channel dimension, wherein each image capture device may generate a hyper-spectrum image having a dimension of 1272×360×6. The resulting stacked image input may then have a dimension of 1272×360×18, wherein the first 6 channels belong to the image capture device 440A, the second 6 channels belong to the image capture devices 440B, and the third 6 channels belong to the image capture device 440C. This stacked image input may be provided to a single deep convolutional neural network (SDNN) 535.

The SDNN 535 is advantageous over known techniques that separately process images from each image capture device via a respective convolutional neural network. That is, if three image capture devices were used, known techniques included three separate convolutional neural networks and three separate statistical analyses to determine HILN. Such techniques are not memory efficient or computationally efficient. In contrast, by stacking the images from the plurality of image capture devices 440A-440O into a single stacked image input and by processing the stacked image inputs with the SDNN 535 as described herein, higher memory and computational efficiency is achieved.

The SDNN 535 may include a segmentation convolutional neural network (SCNN) 536 that receives the stacked image data and simultaneously outputs multiple pixel label maps 537, wherein the number of pixel label maps 537 corresponds to the number of image capture devices (e.g., three, corresponding to the three image capture devices 440A-440O). The SDNN 535 may also include a classification convolutional neural network (CONN) 538 that receives the multiple pixel label maps 537 as input and outputs a determination of HILN 540H, 540I, 540L, 540N. Optionally, the SCNN 536 may output serum segmentation information 542 and/or specimen container/cap type information 544.

Prior to receiving image data from image capture devices 440A-440O for determining HILN (and/or optionally segmentation and/or cap type information), the SDNN 535 may have been previously trained to recognize HILN and optionally serum segmentation and/or specimen container/cap type. In some embodiments, the SCNN 536 may first be trained without the CONN 538. Multiple sets of training examples may be used to train the SCNN 536. The SCNN 536 may be trained by imaging with the quality check module 130 a multitude of samples of specimen containers 102 containing specimen 212 by graphically outlining various regions of a multitude of examples of specimens 212 having various specimen HILN conditions, outlining the various regions of occlusion by label 218, levels of serum or plasma portion 212SP, and the like. Along with the graphical outlines, class characterization information for each area may be provided. As many as 500 or more, 1000 or more, 2,000 or more, or even 5,000 or more images may be used for training the SCNN 536. Each training image may have at least the serum or plasma portion 212SP, its H, I, L, or N identified, various index levels (if output), and the label 218 outlined manually to identify and teach the SCNN 536 the areas that belong to each class that will be a possible output. The SCNN 536 may be tested intermittently with a sample specimen container to see if the SCNN 536 is operating at a sufficiently high level of confidence. If not operating at 100% (e.g., 98% confidence level or more) in determining the correct HILN configuration as an output, then more training samples may be imaged and input along with associated characterization information. In embodiments where segmentation and/or cap type is also provided, the training may involve outlining the segmented classes and/or cap types outputted and including as input class identification information. After training of SCNN 536 alone, CCNN 538 may be added to SCNN 536 and both networks may be additionally trained end-to-end, wherein any segmentation and classification losses can be combined at the end. That is, the loss from the CCNN 538 can be back-propagated to the SCNN 536.

In some embodiments of apparatus 500, the output of the SDNN 535 may be N-class hemolytic 540H, N-class icteric 540I, N-class lipemic 540L, or normal 540N, wherein N-class is the number (N) of class options in that interferent class. As before, stacked multi-view, multi-spectral, multi-exposure consolidated and normalized image data sets may be input into the SDNN 535 and the image data sets may be operated upon and processed by the SCNN 536 and CCNN 538. The output of the processing by the SDNN 535 may be multiple output possibilities (N-classes) for each of HIL, and/or for each viewpoint. For example, N may equal three, wherein the outputs may include H1, H2, and H3 at 540H; I1, I2, and I3 at 540I; and L1, L2, L3 at 540L.

Figure 6:
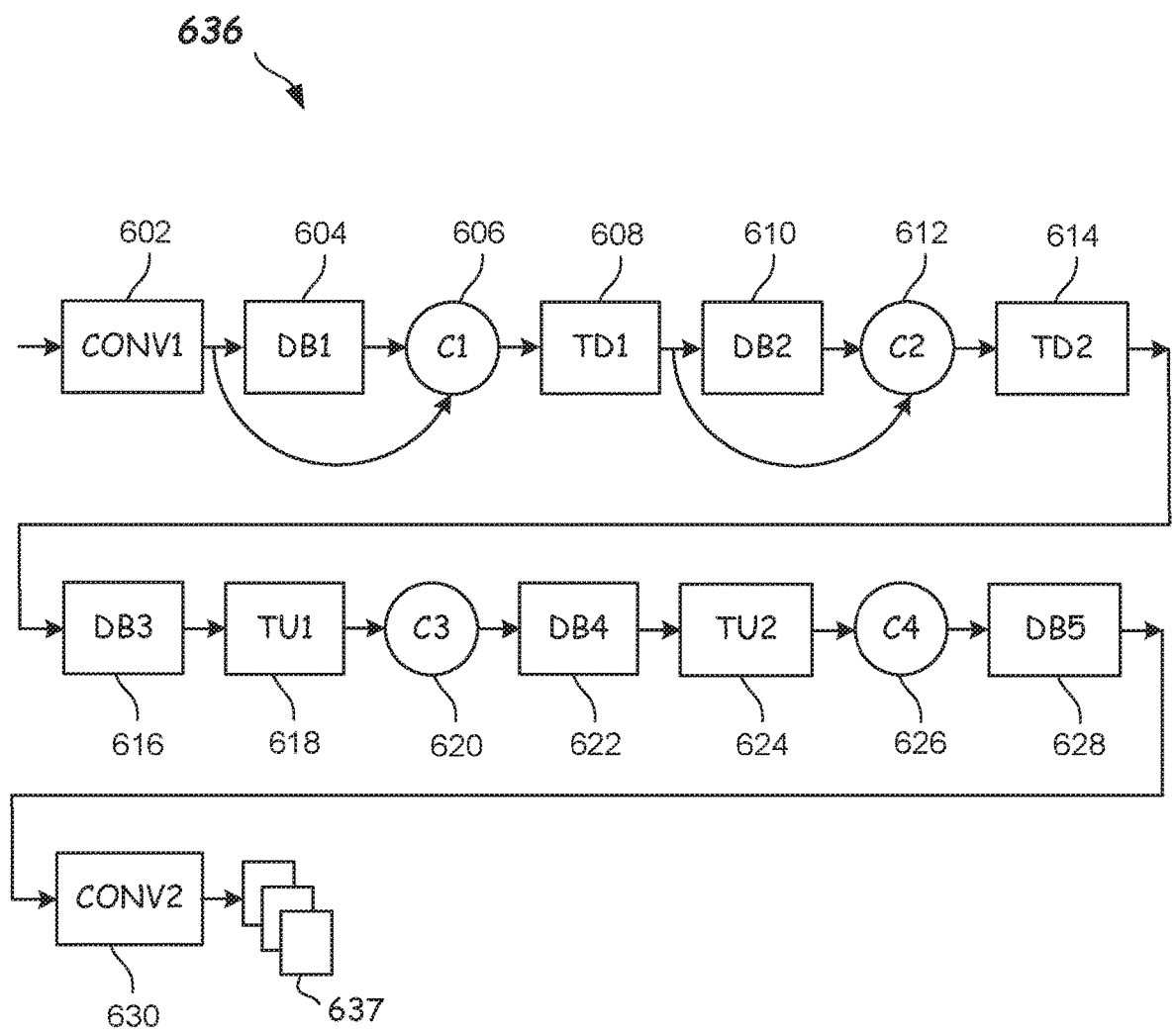
FIG. 6 illustrates a block diagram of an architecture of the segmentation convolutional neural network (SCNN) of FIG. 5 according to one or more embodiments.

FIG. 6 illustrates an architecture 636 of SCNN 536 in accordance with one or more embodiments. SCNN 536 may be coded using any suitable scientific computing framework, program, or toolbox, such as, for example, Caffe available from Berkley Vision and Learning Center (BVLC), Theano, a Python framework for fast computation of mathematical expressions, TensorFlow, Torch, and the like. Architecture 636 may include the following operational layers: two convolutional layers (CONV1 and CONV2) 602 and 630; five dense block layers (DB1-DB5) 604, 610, 616, 622, and 628; four concatenation layers (C1-C4) 606, 612, 620, and 626; two transition down layers (TD1 and TD2) 608 and 614; and two transition up layers (TU1 and TU2), arranged as shown in FIG. 6 wherein multiple pixel label maps 637 are output. Note that the input to each dense block layer 604 and 610 is concatenated (at C1 and C2, respectively) with its output, which may result in a linear growth of the number of pixel label maps. Each dense block layer 604, 610, 616, 622, and 628 may include multiple layers (e.g., 3 or 4), each including a batch normalization operation, a ReLu layer, and a 3×3 convolutional layer with dropout p=0.2. A first layer receives an input and outputs a number of pixel label maps, which are concatenated to the input. A second layer then receives the concatenated output as its input and outputs a number of pixel label maps, which are again concatenated to the previous pixel label maps. This is repeated for each layer in the dense label block. Each transition down layer 608 and 614 may include a batch normalization operation, followed by a ReLu layer, followed by a 1×1 convolutional layer with dropout p=0.2, followed by a 2×2 max pooling layer. Each transition up layer 618 and 624 may include a 3×3 transposed convolutional layer with stride 2.

Figure 7:
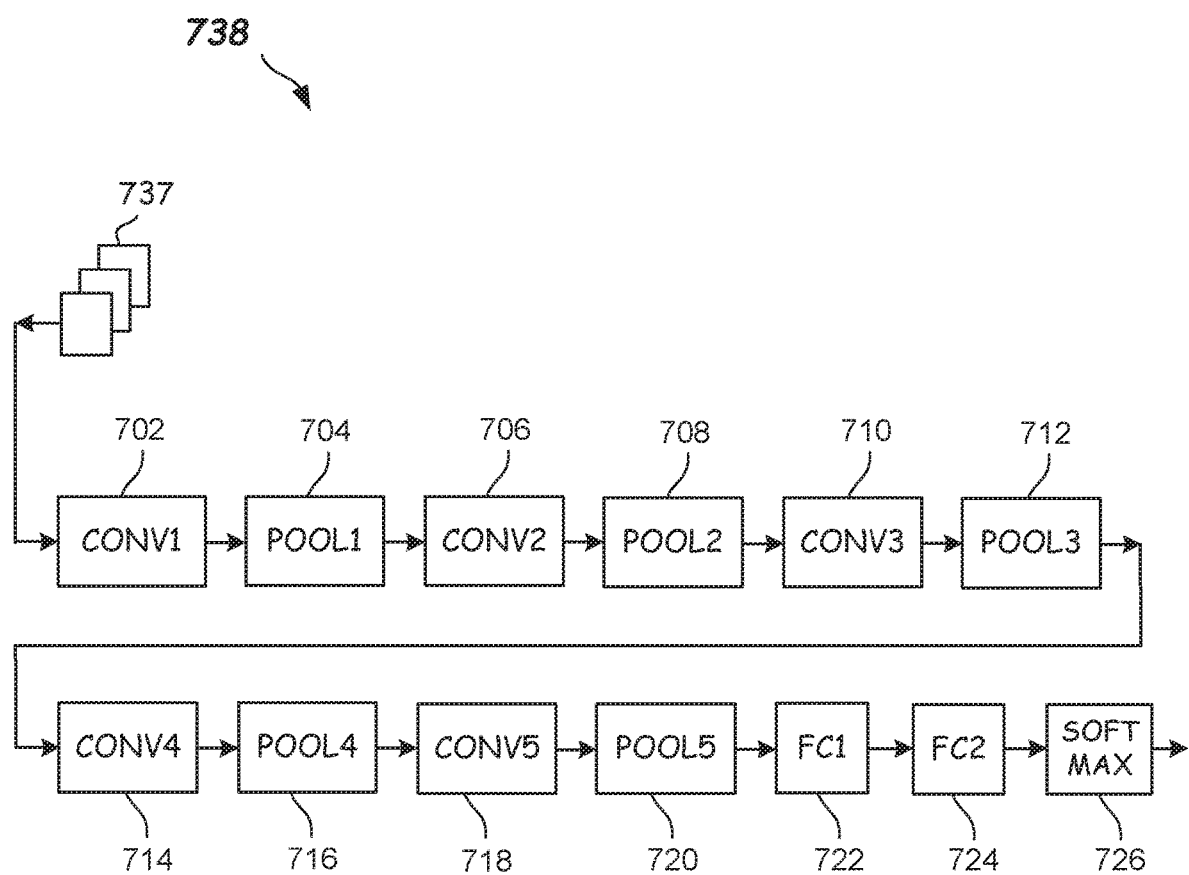
FIG. 7 illustrates a block diagram of an architecture of the classification convolutional neural network (CONN) of FIG. 5 according to one or more embodiments.

FIG. 7 illustrates an architecture 738 of CCNN 538 in accordance with one or more embodiments. CCNN 536 may be coded using any suitable scientific computing framework, program, or toolbox, such as, for example, Caffe available from Berkley Vision and Learning Center (BVLC), Theano, a Python framework for fast computation of mathematical expressions, TensorFlow, Torch, and the like. Architecture 738 may include the following operational layers: five sets of convolutional layers (CONV1-CONV5) 702, 706, 710, 714, and 718 and max pooling layers (POOL1-POOL5) 704, 708, 712, 716, and 720, followed by two fully-connected layers (FC1 and FC2) 722 and 724, followed by a softmax layer 726. Convolutional layer 702 receives as input multiple pixel label maps 737, which may be multiple pixel label maps 537 or 637 (FIGS. 5 and 6, respectively). Convolutional layer 702 may be one or more 3×3 convolutional layers of depth of 64 (i.e., 64 filters). Convolutional layer 706 may be one or more 3×3 convolutional layers of depth of 128 (i.e., 128 filters). Convolutional layer 710 may be one or more 3×3 convolutional layers of depth of 256 (i.e., 256 filters). Convolutional layer 714 may be one or more 3×3 convolutional layers of depth of 512 (i.e., 512 filters). And convolutional layer 718 may be one or more 3×3 convolutional layers also of depth of 512 (i.e., 512 filters). Fully-connected layers 722 and 724 may each be of size 4096, while softmax layer may be of size 1000.

As used herein, a convolution layer is a processing step that may apply a filter (also referred to as a kernel) to input image data (e.g., pixel intensity values) to output an activation map that may indicate detection of some specific type of feature (e.g., from a simple curve after application of a first convolution layer to somewhat more complex features after application of several convolution layers) at some spatial position in the input image data.

A max pooling layer is a processing step that may apply a filter to generate output activation maps having maximum pixel values appearing in the one or more activation maps received from a convolutional layer.

A ReLU (rectified linear unit) layer is a processing step that may apply a nonlinear function to all values in a received activation map resulting in, e.g., all negative activation values being assigned a value of zero.

A fully connected layer is a processing step that aggregates previous activation maps (each of which may indicate detection of lower level features) to indicate detection of higher-level features.

A softmax layer is typically a final processing step that outputs a probability distribution highlighting or identifying the most likely feature of one or more images from a class of image features.

By using a single deep convolutional neural network such as SDNN 535 for receiving image data from all the image capture devices 440A-440C, instead of using a respective convolutional neural network for each image capture device 440A-440C as in some known apparatus, and by attaching a classification convolutional neural network (e.g., CCNN 538 and architecture 738) to the segmentation convolutional neural network (e.g., SCNN 536 and architecture 636), the single deep convolutional neural network design has higher memory and computational efficiency as well as increased system performance as compared to other known convolutional neural networks.

Figure 8:
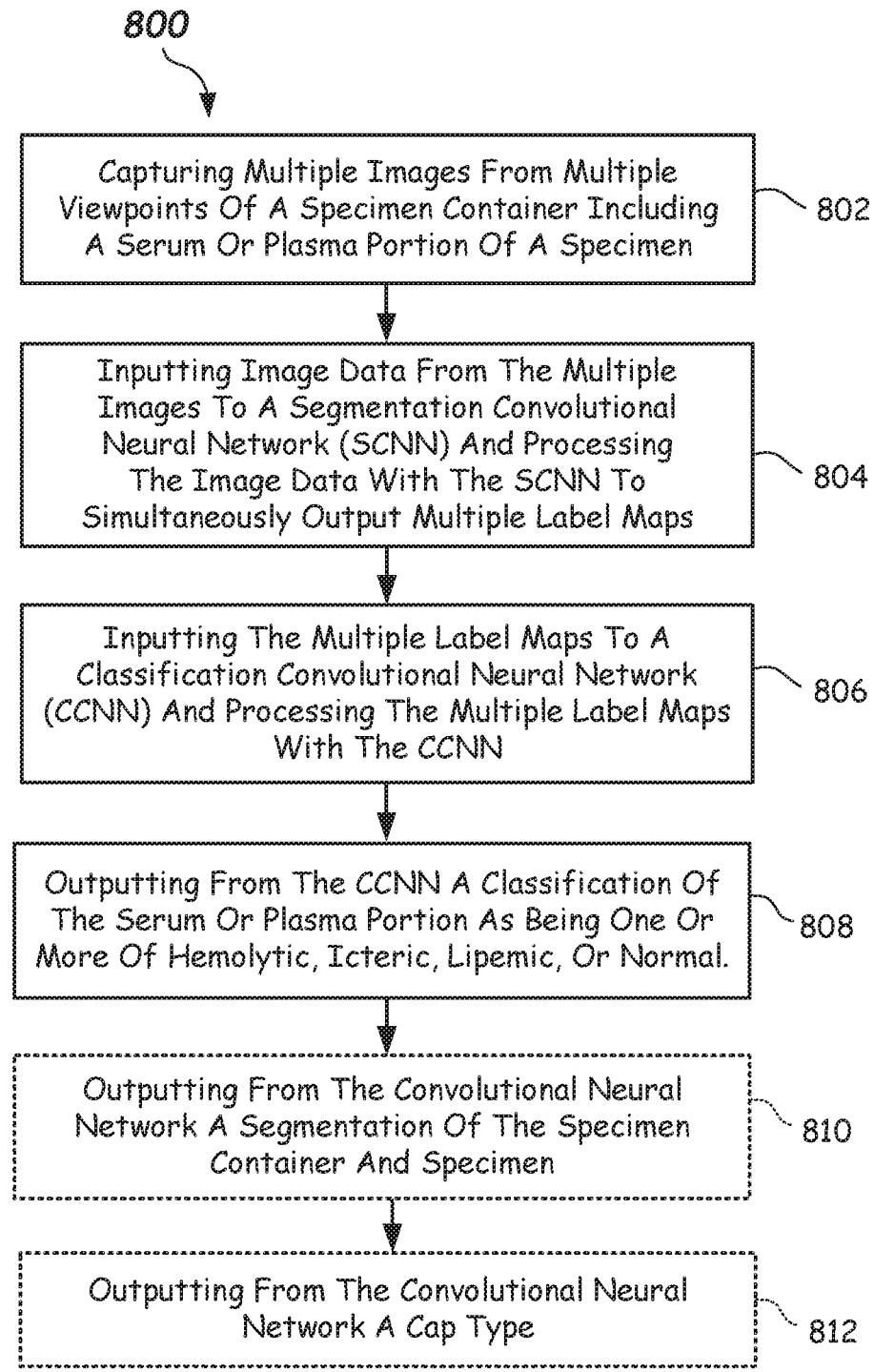
FIG. 8 is flowchart of a method of determining H, I, and/or L, or N in a specimen according to one or more embodiments.

FIG. 8 illustrates a flowchart of a characterization method 800 according to embodiments of the disclosure. The characterization method 800 may be carried out by quality check module 130 as described herein. In particular, the characterization method 800 may determine a presence of an interferent in a specimen 212 according to one or more embodiments. The characterization method 800 includes, in process block 802, capturing multiple images of a specimen container (e.g., specimen container 102) including a serum or plasma portion (e.g., serum or plasma portion 212SP) of a specimen (e.g., specimen 212) from multiple viewpoints (e.g., viewpoints 1, 2, and 3). Moreover, the specimen container 102 may include one or more labels (e.g., label 218) thereon. The one or more images may be digital, pixelated images captured using one or more image capture devices (e.g., image capture devices 440A-4400).

The characterization method 800 further includes, in process block 804, inputting image data (e.g., stacked, consolidated, and normalized image data sets) from the multiple images to a segmentation convolutional neural network (e.g., SCNN 536) and processing the image data with the SCNN to simultaneously output multiple label maps. The processing may be accomplished by the computer 143 described herein after suitable training of the SCNN 536.

In process block 806, the characterization method 800 includes inputting the multiple label maps to a classification convolutional neural network (e.g., CCNN 538) and processing the multiple label maps with the CCNN. The processing may be accomplished by the computer 143 described herein after suitable training of the SCNN 536 and the CCNN 538.

The characterization method 800 further includes, in process block 808, outputting from the classification convolutional neural network (e.g., CCNN 538) a classification of the serum or plasma portion as being one or more of hemolytic, icteric, lipemic, and normal (i.e., H, I, L, H and I, H and L, I and L, H, I, and L, or N).

The multiple images from the multiple viewpoints may be captured at different exposure times and/or at a different spectral illumination (e.g., R, G, B, white light, IR, and/or near IR). For example, there may be 4-8 different exposures or more taken at different exposure times for each viewpoint under the different spectral illumination conditions.

In an optional aspect, in addition to the HILN determination, a segmentation of the image data sets may be obtained. The method 800 may, in process block 810, output from the SCNN (e.g. SCNN 536) a segmentation of the specimen container 102 and specimen 212. The image data may be segmented into N'-classes (e.g., 7 classes), such as (1) Tube, (2) Gel Separator, (3) Cap, (4) Air, (5) Label, (6) Settled Blood Portion, and/or (7) Serum or Plasma Portion. Other numbers of classes may be used.

The characterization method 800 may also optionally include, in process block 812, outputting from the SCNN (e.g., SCNN 536) a cap type (544), which may be a specific cap shape or cap color that was pre-trained into the SCNN 536 and the CONN 538.

Accordingly, based on the foregoing it should be apparent that an improved characterization method 800 is provided that better characterizes the serum or plasma portion 212SP by accounting for labels that may occlude the one or more viewpoints. The improved characterization may be used to provide a rapid and robust characterization of a presence of HILN in the specimen 212, and in some embodiments, an interferent level (H1, H2, H3, I1, I2, I3, L1, L2, L3) may be assessed and output from the CONN 538.

As should be apparent, the above characterization methods may be carried out using a quality check module (e.g., quality check module 130), comprising a plurality of image capture devices (e.g., image capture devices) 440A-440C arranged around an imaging location (e.g., imaging location 432), and configured to capture multiple images from multiple viewpoints (e.g., multiple viewpoints 1-3) of a specimen container 102 including one or more labels 218 and containing a serum or plasma portion 212SP of a specimen 212, and a computer (e.g., computer 143) coupled to the plurality of image capture devices and configured to process image data of the multiple images. The computer (e.g., computer 143) may be configured and capable of being operated to process and stack the multiple images from the multiple viewpoints (e.g., viewpoints 1-3) to provide HILN determination or HILN determination in combination with segmentation for each of the multiple viewpoints.

Further, the characterization method 800 may be carried out on a specimen testing apparatus 100 that includes the quality check module 130. The specimen testing apparatus 100 may include a track 121, and a carrier 122 moveable on the track 121. The carrier 122 may be configured to contain and support the specimen container 102 including the one or more labels 218 and containing a serum or plasma portion 212SP of a specimen 212 and to carry the specimen container 102 to the quality check module 130 to accomplish the characterization and the pre-screening for the presence of an interferent.

While the disclosure is susceptible to various modifications and alternative forms, specific method and apparatus embodiments have been shown by way of example in the drawings and are described in detail herein. It should be understood, however, that the particular methods and apparatus disclosed herein are not intended to limit the disclosure but, to the contrary, to cover all modifications, equivalents, and alternatives falling within the scope of the claims.

What is claimed is:

1. A method of characterizing a specimen container, comprising:
   capturing multiple images of the specimen container from multiple viewpoints, the specimen container including a serum or plasma portion of a specimen therein;
   inputting image data from the multiple images to a segmentation convolutional neural network and processing the image data with the segmentation convolutional neural network to simultaneously output multiple label maps;
   inputting the multiple label maps to a classification convolutional neural network and processing the multiple label maps with the classification convolutional neural network; and
   outputting from the classification convolutional neural network a classification of the serum or plasma portion as being one or more of hemolytic, icteric, lipemic, or normal.

2. The method of claim 1, further comprising training the segmentation convolutional neural network first without the classification convolutional neural network.

3. The method of claim 1, further comprising training the segmentation convolutional neural network and the classification convolutional neural network end-to-end.

4. The method of claim 1, further comprising stacking together a respective captured image from each viewpoint into a single image with additional channels corresponding to the number of viewpoints.

5. The method of claim 1, wherein the image data from the multiple images comprises consolidated pixel or patch data from multiple exposures.

6. The method of claim 1, wherein the number of simultaneously output multiple label maps corresponds to the number of multiple viewpoints.

7. The method of claim 1, wherein the segmentation convolutional neural network comprises an architecture including at least two layers including convolution and pooling, and at least two fully convolution layers.

8. The method of claim 1, wherein the segmentation convolutional neural network comprises an architecture including at least one of a deconvolution layer and a SoftMax layer.

9. The method of claim 1, wherein the classification convolutional neural network comprises a plurality of convolutional layers.

10. The method of claim 1, wherein the classification of the serum or plasma portion comprises output options for N-classes each of hemolytic, icteric, and lipemic.

11. The method of claim 1, wherein the classification convolutional neural network further outputs options for N'-classes of segmentation data.

12. The method of claim 1, wherein the classification convolutional neural network further outputs options for N"-classes of cap types.

13. The method of claim 1, wherein the specimen container includes one or more labels occluding at least part of one viewpoint.

14. A quality check system, comprising:
    a plurality of image capture devices configured to capture multiple images from multiple viewpoints of a specimen container containing a serum or plasma portion of a specimen therein; and
    a computer coupled to the plurality of image capture devices, the computer configured and operative to:
      input image data from the multiple images to a segmentation convolutional neural network and process the image data with the segmentation convolutional neural network to simultaneously output multiple label maps,
      input the multiple label maps to a classification convolutional neural network and process the multiple label maps with the classification convolutional neural network; and
      output from the classification convolutional neural network a classification of the serum or plasma portion as being one or more of hemolytic, icteric, lipemic, or normal.

15. The quality check system of claim 14, wherein the computer is further configured and operative to train the segmentation convolutional neural network first without the classification convolutional neural network.

16. The quality check system of claim 14, wherein the computer is further configured and operative to stack together a respective captured image from each viewpoint into a single image with additional channels corresponding to the number of viewpoints.

17. A specimen testing apparatus, comprising:
    a track;
    a carrier moveable on the track and configured to contain a specimen container containing a serum or plasma portion of a specimen therein;
    a plurality of image capture devices arranged around the track and configured to capture multiple images from multiple viewpoints of the specimen container and the serum or plasma portion of the specimen; and
    a computer coupled to the plurality of image capture devices, the computer configured and operative to:
      input image data from the multiple images to a segmentation convolutional neural network and process the image data with the segmentation convolutional neural network to simultaneously output multiple label maps,
      input the multiple label maps to a classification convolutional neural network and process the multiple label maps with the classification convolutional neural network, and output from the classification convolutional network a classification of the serum or plasma portion as being one or more of hemolytic, icteric, lipemic, or normal.

18. The specimen testing apparatus of claim 17, wherein the computer is further configured and operative to train the segmentation convolutional neural network first without the classification convolutional neural network.

19. The specimen testing apparatus of claim 17, wherein the computer is further configured and operative to stack together a respective captured image from each viewpoint into a single image with additional channels corresponding to the number of viewpoints.

20. The specimen testing apparatus of claim 17, wherein the computer is further configured and operative to output options for N'-classes of segmentation data or options for N"-classes of cap types.

* * * * *